(12) United States Patent
Mizoguchi et al.

(10) Patent No.: US 9,128,161 B2
(45) Date of Patent: Sep. 8, 2015

(54) VOLTAGE MONITORING DEVICE

(75) Inventors: Hayato Mizoguchi, Takahama (JP);
Yasuhiro Kamiya, Toyohashi (JP);
Takumi Shimizu, Yokkaichi (JP)

(73) Assignee: DENSO CORPORATION, Kariya (JP)

( * ) Notice: Subject to any disclaimer, the term of this patent is extended or adjusted under 35 U.S.C. 154(b) by 358 days.

(21) Appl. No.: 13/602,604

(22) Filed: Sep. 4, 2012

(65) Prior Publication Data
US 2013/0057294 A1 Mar. 7, 2013

(30) Foreign Application Priority Data

Sep. 5, 2011 (JP) .................................. 2011-192562

(51) Int. Cl.
| | |
|---|---|
| G01N 27/416 | (2006.01) |
| G01R 31/36 | (2006.01) |
| B60L 1/00 | (2006.01) |

(Continued)

(52) U.S. Cl.
CPC .................. *G01R 31/362* (2013.01); *B60L 1/00* (2013.01); *G01N 1/00* (2013.01); *G01R 1/00* (2013.01); *G01R 31/3658* (2013.01); *H02J 1/00* (2013.01); *B60L 2200/00* (2013.01);

(Continued)

(58) Field of Classification Search
CPC .......... H02J 1/00; B60L 1/00; B60L 2200/00; B60L 2210/00; G01N 1/00; G01N 2201/00; G01N 2203/00; G01R 1/00
USPC .......... 320/116, 120, 121, 151, 152, 156, 157, 320/159, 161–165; 324/434, 72, 72.5
See application file for complete search history.

(56) References Cited

U.S. PATENT DOCUMENTS

| | | | |
|---|---|---|---|
| 6,437,722 B1 * | 8/2002 | Yoshizawa | .................... 341/154 |
| 7,397,221 B2 * | 7/2008 | Sakuma et al. | ............... 320/134 |

(Continued)

FOREIGN PATENT DOCUMENTS

| | | |
|---|---|---|
| JP | 2002-289263 A | 10/2002 |
| JP | 2002-291167 A | 10/2002 |

(Continued)

OTHER PUBLICATIONS

Office Action (2 pages) dated Aug. 27, 2013, issued in corresponding Japanese Application No. 2011-192562 and English translation (2 pages).

(Continued)

*Primary Examiner* — Huy Q Phan
*Assistant Examiner* — Temilade S Rhodes-Vivour
(74) *Attorney, Agent, or Firm* — Nixon & Vanderhye P.C.

(57) ABSTRACT

A voltage monitoring device monitors voltage of each of battery cells connected in series to one another to configure an assembled battery. The device includes a capacitor circuit, a filter circuit, an input side connection switching unit, a potential difference detection unit, and an output side connection switching unit. The capacitor circuit includes a plurality of capacitors connected in series to one another. The filter circuit includes a plurality of resistors connected to an electrode terminal of each of the battery cells. The plurality of resistors are divided into a first resistor group and a second resistor group. The first resistor group is connected to a connection point between adjacent capacitors of the plurality of capacitors. The second resistor group is connected to an independent end of the plurality of capacitors. A resistance value of the first resistor group is smaller than a resistance value of the second resistor group.

10 Claims, 7 Drawing Sheets

(51) Int. Cl.
*H02J 1/00* (2006.01)
*G01R 1/00* (2006.01)
*G01N 1/00* (2006.01)

(52) U.S. Cl.
CPC ........ *B60L 2210/00* (2013.01); *G01N 2201/00* (2013.01); *G01N 2203/00* (2013.01)

(56) References Cited

U.S. PATENT DOCUMENTS

| | | | |
|---|---|---|---|
| 7,402,982 B2* | 7/2008 | Ito et al. | 320/150 |
| 8,188,750 B2 | 5/2012 | Ohnuki | |
| 2003/0067221 A1* | 4/2003 | Disser et al. | 307/10.1 |
| 2004/0051534 A1* | 3/2004 | Kobayashi et al. | 324/429 |
| 2008/0079393 A1* | 4/2008 | Spartano et al. | 320/110 |
| 2009/0039830 A1* | 2/2009 | Pellenc | 320/116 |
| 2010/0091529 A1* | 4/2010 | Jakeman et al. | 363/36 |
| 2010/0134115 A1 | 6/2010 | Ohnuki | |
| 2011/0121656 A1* | 5/2011 | Hicks et al. | 307/80 |
| 2011/0285539 A1 | 11/2011 | Lee et al. | |
| 2012/0173059 A1* | 7/2012 | Andris | 701/22 |

FOREIGN PATENT DOCUMENTS

| | | |
|---|---|---|
| JP | 2002-315212 A | 10/2002 |
| JP | 2002-357624 A | 12/2002 |
| JP | 2003-014792 A | 1/2003 |
| JP | 2003-084015 A | 3/2003 |
| JP | 2004-245743 A | 9/2004 |
| JP | 2006-078323 A | 3/2006 |
| JP | 2007-240299 | 9/2007 |
| JP | 2010-181168 | 8/2010 |
| WO | WO 2011/102576 | 8/2011 |

OTHER PUBLICATIONS

Office Action (1page) dated Jul. 15, 2014, issued in corresponding Japanese Application No. 2011-192562 and English translation (2 pages).

Office Action (2 pgs.) dated Nov. 5, 2013 in corresponding Japanese Application No. 2011-192562 with an at least partial English-language translation thereof (2 pgs.).

* cited by examiner

TIME CONSTANT $\tau 2$: $(R+R/2) \times C = 1.5RC$

TIME CONSTANT $\tau 3$: $(R+R) \times C = 2RC$

VOLTAGE MONITORING DEVICE

CROSS-REFERENCE TO RELATED APPLICATION

This application is based on and claims the benefit of priority from earlier Japanese Patent Application No. 2011-192562 filed Sep. 5, 2011, the description of which is incorporated herein by reference.

BACKGROUND OF THE INVENTION

1. Technical Field of the Invention

The present invention relates to a voltage monitoring device, and in particular, to a voltage monitoring device using a flying capacitor method, which monitors voltage of each of battery cells connected in series to one another to configure an assembled battery by using a plurality of capacitors.

2. Related Art

In related art, a device using a capacitor is proposed as a voltage monitoring device that monitors voltage of each of battery cells connected in series to one another to configure an assembled battery, e.g., an in-vehicle high voltage battery mounted in vehicles such as hybrid vehicles or electric vehicles. This device is also called a voltage monitoring device using a flying capacitor method or a flying capacitor type voltage monitoring device.

For example, JP-A-2002-289263 discloses a voltage monitoring device using a flying capacitor method, which detects voltages of two adjacent battery cells in the assembled battery by using a pair of capacitors connected in series to each other. This flying capacitor method using a pair of capacitors is also called as a double flying capacitor method.

The device using the flying capacitor method is provided with a resistor functioning as a filter between each of the battery cells and the capacitor. Depending on a resistance value of the resistor and a capacitance value of the capacitor, a time (time constant) required for the capacitor to be charged with voltage of the battery cell varies.

In the device using the double capacitor method disclosed in JP-A-2002-289263, the pair of capacitors are connected in series to each other, and therefore, total capacitance of the capacitors becomes smaller in charging the capacitors with voltage of the battery cell. This can shorten a time for required for the capacitor to be charged by voltage of the battery cell, when the pair of capacitors are used for detecting voltage of the battery cell, compared to when only one capacitor is used for detecting voltage of the battery cell.

Additionally, in the double capacitor method, each of the capacitors is charged with voltage of the same battery cell to compare charged voltage of each of the capacitors with each other, thereby being able to detect, e.g., disconnection of detection lines which connect each of the capacitors and each of the battery cells.

On the other hand, the device using the double capacitor method disclosed in JP-A-2002-289263 may detect voltage of the battery cell by using not only both of the capacitors but also one thereof.

For example, when voltage of the battery cell is detected by using the pair of capacitors, current does not flow in a detection line connected to a connection point between each of capacitors among a plurality of detection lines connecting each of the capacitors and each of the battery cells. In this case, if this detection line is disconnected, this disconnection cannot be detected. Due to this, voltages of the battery cells may be detected individually by using one of the pair of capacitors.

However, in using one of the pair of capacitors, if a resistance value of each of the plurality of resistors functioning as the filter are the same value, total capacitance of the capacitors becomes larger compared to using both of the pair of capacitors. This results in an increase in a time for required for the capacitor to be charged with voltage of the battery cell.

As one resolution to shorten a time for required for the capacitor to be charged with voltage of the battery cell in using one of the pair of capacitors, all of the resistors functioning as the filter may have the same resistance value. In this case, a filter function of each of the resistors may be damaged.

The same issue explained above may occur in a voltage monitoring device using a flying capacitor method which is configured to detect voltage of each of a plurality of battery cells using three or more capacitors.

SUMMARY

It is thus desired to provide a voltage monitoring device using a flying capacitor method which monitors voltage of each of battery cells of an assembled battery by using a plurality of capacitors, and which is able to avoid a decrease in a filter function of each of resistors and to shorten a time for required for the capacitor to be charged with voltage of the battery cell.

According to an exemplary aspect of the present disclosure, there is provided a voltage monitoring device for monitoring voltage of each of battery cells connected in series to one another to configure an assembled battery, comprising: a capacitor circuit that includes a plurality of capacitors connected in series to one another; a filter circuit that includes a plurality of resistors connected to an electrode terminal of each of the battery cells; an input side connection switching unit that connects the electrode terminal of each of the battery cells to an independent end of the plurality of capacitors and a connection point between adjacent capacitors among the plurality of capacitors via the filter circuit to apply voltage of each of the battery cells to the capacitors; a potential difference detection unit that includes a plurality of input terminals and detects a potential difference between the plurality of input terminals; an output side connection switching unit that connects the independent end of the plurality of capacitors and the connection point between the adjacent capacitors to the plurality of input terminals to apply charged voltage of at least one capacitor among the plurality of input terminals to the plurality of input terminals of the potential difference detection unit, wherein: the plurality of resistors is divided into a first resistor group and a second resistor group; the first resistor group is connected to the connection end between the adjacent capacitors; the second resistor group is connected to the independent end of the plurality of capacitors; and a resistance value of the first resistor group is smaller than a resistance value of the second resistor group.

Thus, among the plurality of resistors of the filter circuit, the resistance value of the first resistor group, which is connected to the connection point between the adjacent capacitors of the plurality of capacitors, is designed to be smaller. This makes it possible to avoid a decrease in a filter function of the filter circuit, compared to a case where the resistance value of all of the resistors of the filter circuit becomes smaller.

In addition, when voltage of the battery cell is applied (charged) to a part of the plurality of capacitors, as the resistance value of the resistors of the first resistor group, which is connected to the connection point between the adjacent capacitors of the plurality of capacitors, becomes smaller, a time for required for the capacitor to be charged with voltage of the battery cell can be more shortened.

In the exemplary aspect, the plurality of capacitors of the capacitor circuit may be configured by a pair of capacitors connected in series to each other.

DETAILED DESCRIPTION OF THE PREFERRED EMBODIMENTS

Figure 1:
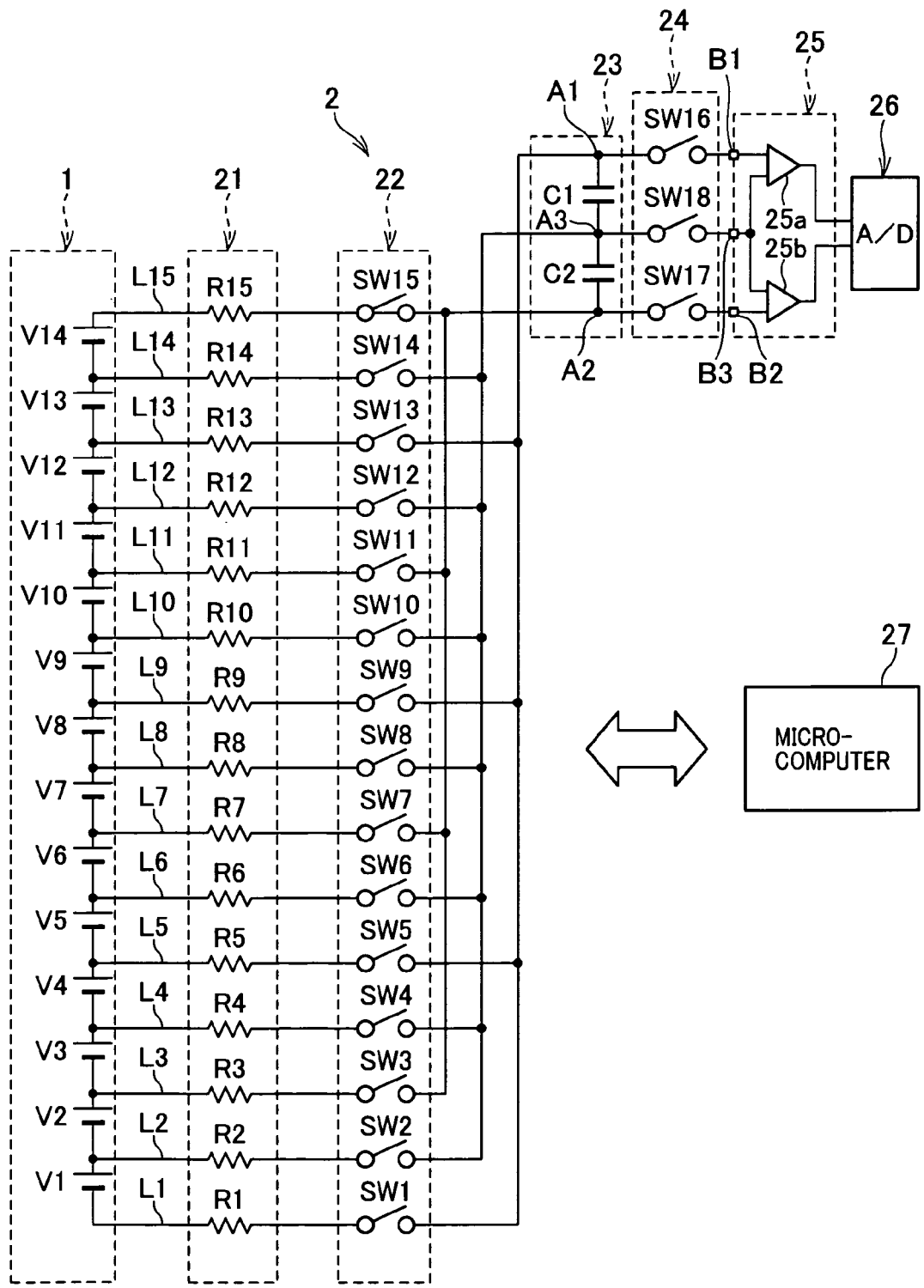
FIG. 1 is a circuit diagram showing an overall configuration of a battery voltage monitoring system including a voltage monitoring device according to a first embodiment of the present invention.

With reference to the accompanying drawings, hereinafter are described some embodiments of the present invention. In the following embodiments and modifications, the components identical with or similar to each other are given the same reference numerals or their equivalents for the sake of omitting unnecessary explanation.

(First Embodiment)

Referring to FIGS. 1 to 5, a first embodiment of the present invention is described, FIG. 1 is a diagram illustrating an overall configuration of a battery voltage monitoring system including a voltage monitoring device 2 according to a first embodiment of the present invention.

The voltage monitoring device 2 in the present embodiment is applied to an in-vehicle high voltage battery configuring an assembled battery 1. For, example, this assembled battery 1 supplies power via an inverter (not shown) to a motor for vehicle running (motor for running).

As shown in FIG. 1, the battery voltage monitoring system in the present embodiment includes, as its main elements, the assembled battery 1 and the voltage monitoring device 2.

The assembled battery 1 is configured by a series connection of n (n=14 in the present embodiment) battery cells V1 to V14 which are connected in series to one another. Lithium-ion battery, lead battery or the like are used as the battery cells V1 to V14.

The assembled battery 1 as configured above is connected to the voltage monitoring device 2 via a plurality of detection lines L1 to L15 which are each connected in series with an electrode terminal (positive or negative electrode terminals) of a respective one of the battery cells.

Next, the voltage monitoring device 2 is described. The voltage monitoring device 2 is a device (voltage monitoring device using a double flying capacitor method) which detects voltage of each of the battery cells V1 to V14 of the assembled battery 1 by using a pair of capacitors (hereinafter referred to as a first and second capacitors) C1 and C2 connected in series to each other to configure a capacitor circuit explained below.

The voltage monitoring device 2 includes a filter circuit 21, an input side connection switching unit 22, a capacitor circuit 23, an output side connection switching circuit 24 (configuring an output side connection switching unit), a potential difference detection circuit 25 (configuring a potential difference detection unit), an analog-to-digital (AD) converter 26, and a microcomputer 27.

The filter circuit 21 is configured by a plurality of resistors R1 to R15 which functions as a filter. Each of the resistors R1 to R15 is connected via each of the detection lines L1 to L15 to an electrode terminal of each of the battery cells V1 to V14. A resistance value of each of the resistors R1 to R15 of the filter circuit 21 will be described below.

The input side connection switching unit 22 is a switching circuit that sequentially connects, via the resistors R1 to R15 of the filter circuit 21, the electrode terminal of each of the battery cells V1 to V14 to an independent end A1 of the first capacitor circuits C1, an independent end A2 of the second capacitor circuits C2, and a connection point A3 between the first and second capacitor circuits C1 and C2. The input side connection switching unit 22 is operated to allow voltage of each of the battery cells V1 to V14 to be applied to the first and second capacitors C1 and C2.

The input side connection switching unit 22 is configured by including a plurality of input side sampling switches SW1 to SW15 which are connected to the resistors R1 to R15 of the filter circuit 21.

Specifically, among the input side sampling switches SW1 to SW15 of the input side connection switching unit 22, the input side electrode terminals SW1, SW5, SW9, and SW13, which are connected to the 4m+1-th electrode terminal (m=0 or positive integer) when the electrode terminal of each of the battery cells V1 to V14 is sequentially numbered in order from the low potential side, are connected to the independent end A1 of the first capacitor C1.

In addition, among the input side sampling switches SW1 to SW15 of the input side connection switching unit 22, the input side electrode terminals SW3, SW7, SW11, and SW15, which connected to "4 m+3-th (m=0 or positive integer)" numbered electrode terminals when the electrode terminal of each of the battery cells V1 to V14 is sequentially numbered in order from the low potential side, are connected to the independent end A2 of the second capacitor C2.

Further, among the input side sampling switches SW1 to SW15 of the input side connection switching unit 22, the input side electrode terminals SW2, SW4, SW6, SW8, SW10, SW12 and SW14, which connected to "2m-th (m=0 or positive integer)", i.e., even numbered electrode terminals when the electrode terminal of each of the battery cells V1 to V14 is sequentially numbered in order from the low potential side, are connected to the connection point A3 between the first and second capacitors C1 and C2.

The input side sampling switches SW1 to SW15 are configured by a semiconductor switch and is controlled to be turned on and off by an instruction signal from the microcomputer 27.

For example, when the capacitors C1 and C2 are charged with voltages of the battery cells V1 and V2, the input side sampling switches SW1 to SW3 of the input side connection switching unit 22 are simultaneously turned on. Thus, the electrode terminal of the battery cell V1 is connected to both ends (the independent end A1 and the connection point A3), and the electrode terminal of the battery cell V2 is connected to both ends (the independent end A2 and the connection point A3). In this way, the first capacitor C1 is charged with voltage of the battery cell V1, and the first capacitor C2 is charged with voltage of the battery cell V2.

The capacitor circuit 23 is configured by a pair of capacitors (first and second capacitors) C1 and C2 connected in series to each other as described above. The first and second capacitors C1 and C2, which are adopted in the present embodiment, have the same capacitance. In the capacitor circuit 23, a contact point between both of the capacitors C1 and C2, i.e., one end of each thereof correspond to the connection point A3, and the other side of the connection point A3, i.e., the other end of each of the capacitors C1 and C2 correspond to the independent ends A1 and A2.

The output side connection switching circuit 24 is a switching circuit that connects the independent ends A1, A2 and the connection point A3 in the capacitors C1 and C2 with a first to third input terminals B1 to B3 provided in the potential difference detection circuit 25. The output side connection switching circuit 24 is operated to allow charged voltage (amount of charge) in at least one of the capacitors C1 and C2 to be applied to the potential difference detection circuit 25.

Specifically, the output side connection switching circuit 24 is configured by including first to third output side sampling switches SW16 to SW18. The first output side sampling switch SW16 is connected to the independent end A2 of the first capacitor C1 and to the first input terminal B1 of the potential difference detection circuit 25. The second output side sampling switch SW17 is connected to the independent end A2 of the second capacitor C2 and to the second input terminal B2 of the potential difference detection circuit 25. The third output side sampling switch SW18 is connected to the connection point A3 between the first and second capacitors C1, C2 and to the third input terminal B3 of the potential difference detection circuit 25.

The output side sampling switches SW16 to SW18 are configured by a semiconductor switch and is controlled to be turned on and off by an instruction signal from the microcomputer 27.

For example, when charged voltage of each of the first and second capacitors C1 and C2 is applied to the potential difference detection circuit 25, the output side sampling switches SW16 to SW18 are turned on. Thus, the independent end A1 and the first input terminal B1 are connected to each other, the independent end A2 and the second input terminal B2 are connected to each other, and the connection point A3 and the third input terminal B3 are connected to each other. In this way, charged voltage of each of the first and second capacitors C1 and C2 is applied to the potential difference detection circuit 25.

In addition, when charged voltage of only the first capacitor C1 is applied to the potential difference detection circuit 25, the output side sampling switches SW16 and SW18 are turned on. Thus, the independent end A1 and the first input terminal B1 are connected to each other, and the connection point A3 and the third input terminal B3 are connected to each other. In this way, charged voltage of each of only the first capacitor C1 is applied to the potential difference detection circuit 25.

Further, when charged voltage of only the second capacitor C2 is applied to the potential difference detection circuit 25, the output side sampling switches SW17 and SW18 are turned on. Thus, the independent end A2 and the second input terminal B2 are connected to each other, and the connection point A3 and the third input terminal B3 are connected to each other. In this way, charged voltage of each of only the second capacitor C2 is applied to the potential difference detection circuit 25.

The potential difference detection circuit 25 is provided with the first to third input terminals B1 to B3. The first terminal B1 is connected to the independent end A1 of the first capacitor C1. The second terminal B2 is connected to the independent end A2 of the second capacitor C2. The third terminal B3 is connected to the connection terminal A3 between the first and second capacitors C1 and C2.

The potential difference detection circuit 25 includes first and second differential voltage detection units 25a and 25b. The first differential voltage detection unit 25a detects a potential difference between the first and second input terminals B1 and B2. The second differential voltage detection unit 25b detects a potential difference between the second and third input terminals B2 and B3. In the present embodiment, the first differential voltage detection unit 25a is configured by a differential amplifier circuit that amplifies charged voltage in the first capacitor C1 to output the amplified voltage. The second differential voltage detection unit 25b is configured by a differential amplifier circuit that amplifies charged voltage in the second capacitor C2 to output the amplified voltage.

The AD converter (A/D) 25 reads voltage signal (analog signal) output from the potential difference detection circuit 25 at a predetermined timing, and converts the read voltage signal to the corresponding digital signal to thereby output the converted digital signal to a side of the microcomputer 27.

The microcomputer 27 is configured by including a central processing unit (CPU), a read only memory (ROM), an electrically erasable programmable ROM (EEPROM), and a random access memory (RAM), and configures a control unit that performs various processes according to programs such as control programs stored in a storage unit such as the ROM.

In the present embodiment, the microcomputer 27 controls an operation of each of the input side sampling switches SW1 to SW15 and each of the output sampling switches SW16 to SW18 according to the control programs stored in the storage unit.

In addition, according to the digital signal output from the AD converter 15, the microcomputer 27 performs a voltage diagnosis process to evaluate a voltage stage of each of the battery cells V1 to V14 and a fault diagnosis process to evaluate a fault such as a disconnection of each of the detection lines L1 to L15.

Next, the resistance value of each of the resistors R1 to R15 is described. In the present embodiment, the resistors R1 to R15 of the filter circuit 21 are divided into two groups: a first resistor group (resistors R2, R4, R6, R8, R10, R12, and R14) and a second resistor group (resistors R1, R3, R5, R7, R9, R11, R13, and R15). The first resistor group is connected the connection point A3 between the first and second capacitors C1 and C2 via the input side connection switching unit 22. The second resistor group is connected to the independent ends A1 and A2 via the input side connection switching unit 22. The first resistor group is configured to be lower in resistance value than the second resistor group.

The first resistor group is configured by, among the resistors R1 to R15, the resistors R2, R4, R6, R8, R10, R12, and R14 which are connected to odd [(2 m+1)-th (m=0 or positive integer)] numbered electrode terminals when the electrode terminal of each of the battery cells V1 to V14 is sequentially numbered in order from the low potential side.

The second resistor group is configured by, among the resistors R1 to R15, the resistors R1, R3, R5, R7, R9, R11, R13, and R15 which are connected to even [2m-th (m=positive integer)] numbered electrode terminals when the electrode terminal of each of the battery cells V1 to V14 is sequentially numbered in order from the low potential side.

Here, it is preferable that a resistance value Rx of each of the resistors R2, R4, R6, R8, R10, R12, and R14 of the first resistor group is designed to be approximate one half of a resistance value Ry of each of the resistors R1, R3, R5, R7, R9, R11, R13, and R15 of the second resistor group (Rx≈Ry/2: Rx is approximately equal to Ry/2), for the purpose of ensuring filter performance of the filter circuit 21 or the like.

In the present embodiment, the resistance value Rx of each of the resistors R2, R4, R6, R8, R10, R12, and R14 of the first resistor group is set to one half of the resistance value Ry of each of the resistors R1, R3, R5, R7, R9, R11, R13, and R15 of the second resistor group (Rx=Ry/2). The resistors R2, R4, R6, R8, R10, R12, and R14 of the first resistor group, which are adopted in the present embodiment, have the same resistance value. The resistors R1, R3, R5, R7, R9, R11, R13, and R15 of the second resistor group, which are adopted in the present embodiment, have the same resistance value.

Next, an operation of the voltage monitoring device 2 in the present embodiment is described. In the present embodiment, the voltage monitoring device 2 uses both of the pair of capacitors C1 and C2 when a voltage monitoring for each of the battery cells V1 to V14 is performed, and uses one of the capacitors C1 and C2 when a fault diagnosis for each of the battery cells V1 to V14 is performed.

Figure 2:
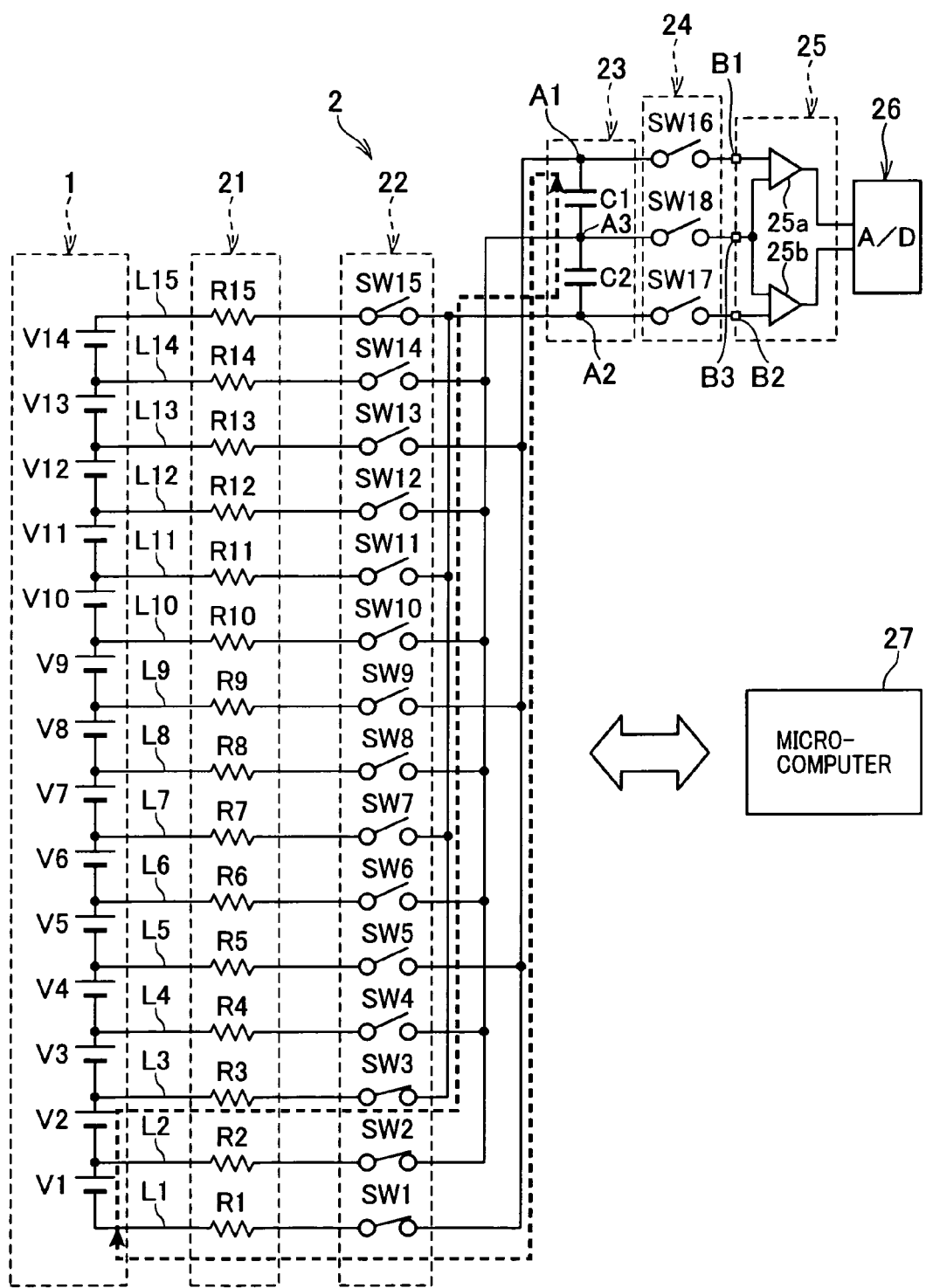
FIG. 2 is a circuit diagram explaining an operation in applying voltage of a battery cell to a pair of capacitors in the voltage monitoring device in FIG. 1.

First, the following case is described. This is a case of performing voltage monitoring for each of the battery cells V1 to V14 by using both of the capacitors C1 and C2 of the capacitor circuit 23. Referring to FIG. 2, an example of an operation in a case where voltage monitoring for four battery cells V1 to V4 is performed by using both of the capacitors C1 and C2 is described in detail. In the example, the four battery cells V1 to V4 are sequentially monitored in order from the low voltage side, i.e., in the order from the battery cells V1, V2, V3, V4, etc.

As shown in FIG. 2, the input side sampling switches SW1 to SW3 of the input side connection switching unit 22 are turned on by the instruction signal from the microcomputer 27. When the input side sampling switches SW1 and to SW2 are turned on, the first capacitor C1 is connected via the resistors R1 and R2 to the electrode terminal of the battery cell V1 to be charged, so that voltage of the first capacitor C1 is equal to that of the battery cell V1. When the input side sampling switches SW2 and to SW3 are turned on, the second capacitor C2 is connected via the resistors R2 and R3 to the electrode terminal of the battery cell V2 to be charged, so that voltage of the second capacitor C2 is equal to that of the battery cell V2.

After that, the input side sampling switches SW1 to SW3 of the input side connection switching unit 22 are turned off and the output side sampling switches SW16 to SW18 of the output side connection switching circuit 24 are turned on for a predetermined duration of time by the instruction signal from the microcomputer 27.

When the output side sampling switches SW16 and SW18 are turned on, the first capacitor C1 is connected to the first differential voltage detection unit 25a via the first and third input terminals B1 and B3 of the potential difference detection circuit 25. The first differential voltage detection unit 25a amplifies voltage of the first capacitor C1, which is equal to that of the battery cell V1, to output the amplified voltage to the AD converter 26.

When the output side sampling switches SW17 and SW18 are turned on, the second capacitor C2 is connected to the second differential voltage detection unit 25b via the second and third input terminals B2 and B3 of the potential difference detection circuit 25. The second differential voltage detection unit 25b amplifies voltage of the second capacitor C2, which is equal to that of the battery cell V2, to output the amplified voltage to the AD converter 26.

The AD converter 26 converts the outputted signals from the first and second differential voltage detection units 25a and 25b to the corresponding digital signals, and outputs the converted digital signals to the microcomputer 27.

Based on the outputted signals from the AD converter 26, the microcomputer 27 detects voltage of each of the battery cells V1 and V2. This makes it possible to determine whether or not abnormality such as excessive charge and discharge or deterioration of the battery cells V1 and V2 is present.

Next, the input side sampling switches SW4 to SW6 of the input side connection switching unit 22 are turned on by the instruction signal from the microcomputer 27. Thus, the first capacitor C1 is connected via the resistors R4 and R5 to the electrode terminal of the battery cell V3 to be charged, so that voltage of the first capacitor C1 is equal to that of the battery cell V3. The second capacitor C2 is connected via the resistors R5 and R6 to the electrode terminal of the battery cell V4 to be charged, so that voltage of the second capacitor C2 is equal to that of the battery cell V4.

After that, the input side sampling switches SW4 to SW6 of the input side connection switching unit 22 are turned off and the output side sampling switches SW16 to SW18 are turned on for a predetermined duration by the instruction signal from the microcomputer 27. Thus, the first capacitor C1 is connected to the first differential voltage detection unit 25a of the potential difference detection circuit 25, and the second capacitor C2 is connected to the second differential voltage detection unit 25b of the potential difference detection circuit 25. Then, voltages of the first and second capacitors C1 and C2 are amplified by the first and second differential voltage detection units 25a and 25b to be outputted to the AD converter 26. The outputted voltages are converted to the corresponding digital signals by the AD converter 26 to be outputted to microcomputer 27.

Based on the outputted signals from the AD converter 26, the microcomputer 27 detects voltage of each of the battery cells V3 and V4. This makes it possible to determine whether or not abnormality such as excessive charge and discharge or deterioration of the battery cells V3 and V4 is present.

When voltage monitoring for the battery cells V5 to V14 other than the battery cells V1 to V4 is performed, the input side sampling switches (among the input side sampling switches SW5 to SW15), which are connected to the battery cells which are voltage detection objects among the battery cells V5 to V14, and the output side sampling switch SW16 to SW18 are controlled to be turned on and off by the instruction signal from the microcomputer 27. This makes it possible to output the digital signal indicating voltage of the battery cells which are voltage detection objects to the microcomputer 27.

Here, for example, when voltages of the adjacent battery cells V1 and V2 are charged in the capacitors C1 and C2, the input side sampling switches of the input side connection switching unit 22 are turned on to form a closed circuit in which the resistors R1 and R3 of the filter circuit 21 and the first and second capacitors C1 and C2 of the capacitor circuit 23 are connected in series to one another. Thus, current flows in this closed circuit as shown by a heavy dotted line and arrow in FIG. 2.

In this way, when voltages of the adjacent battery cells V1 and V2 are charged in the capacitors C1 and C2, the pair of the capacitors C1 and C2 are connected in series to each other. Due to this, a capacitance of the capacitors in the closed circuit is determined by the harmonic mean of a capacitance value of the first capacitors C1 and a capacitance value of the second capacitor C2. Thus, the total capacitance value in the closed circuit becomes smaller. This makes it possible to shorten a time for the capacitor to be charged with voltage of the battery cell.

Figure 3:
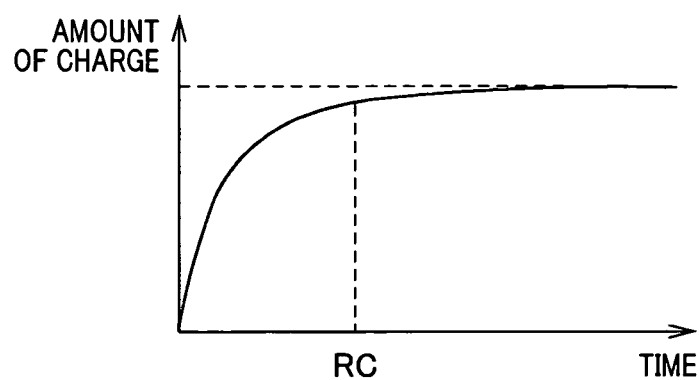
FIG. 3 is a graph explaining a time required for a pair of capacitors to be charged with voltage of a battery cell in the voltage monitoring device in FIG. 1

That is, in a case where voltage monitoring for the battery cells V1 and V2 by using the pair of capacitors C1 and C2, when the input side sampling switches SW1 and SW2 are turned on, as shown in FIG. 3, the capacitors C1 and C2 are charged under a condition of time constant $\tau 1$ (=RC). As shown in a formula in FIG. 3, this time constant $\tau 1$ is a value (=(R+R)×C/2=RC) which is determined by multiplying a harmonic mean value (=1/(1/C+1/C)=C/2) of a capacitance value (=C) of the first capacitor C1 and a capacitance value (=C) of the second capacitor C2 by an addition value (=R+R=2R) which is determined by addition of a resistance value Ry (=R) of the resistor R1 of the second resistor group and a resistance value Ry (=R) of the resistor R3 of the second resistor group.

As shown in a heavy dotted arrow in FIG. 2, current does not flow in the resistor R2 of the first resistor group. Due to this, time constant $\tau 1$ is not influenced by a resistance value Rx (=R/2).

In the present embodiment, an example in which the capacitors C1 and C1 are charged with voltages of the adjacent battery cells V1 and V2 is explained. The same is applied to a case where the capacitors C1 and C1 are charged with voltages of the adjacent battery cells other than the battery cells V1 and V2. In this case, the capacitors C1 and C1 are charged under a condition of time constant $\tau 1$ (=RC) as described above.

Figure 4:
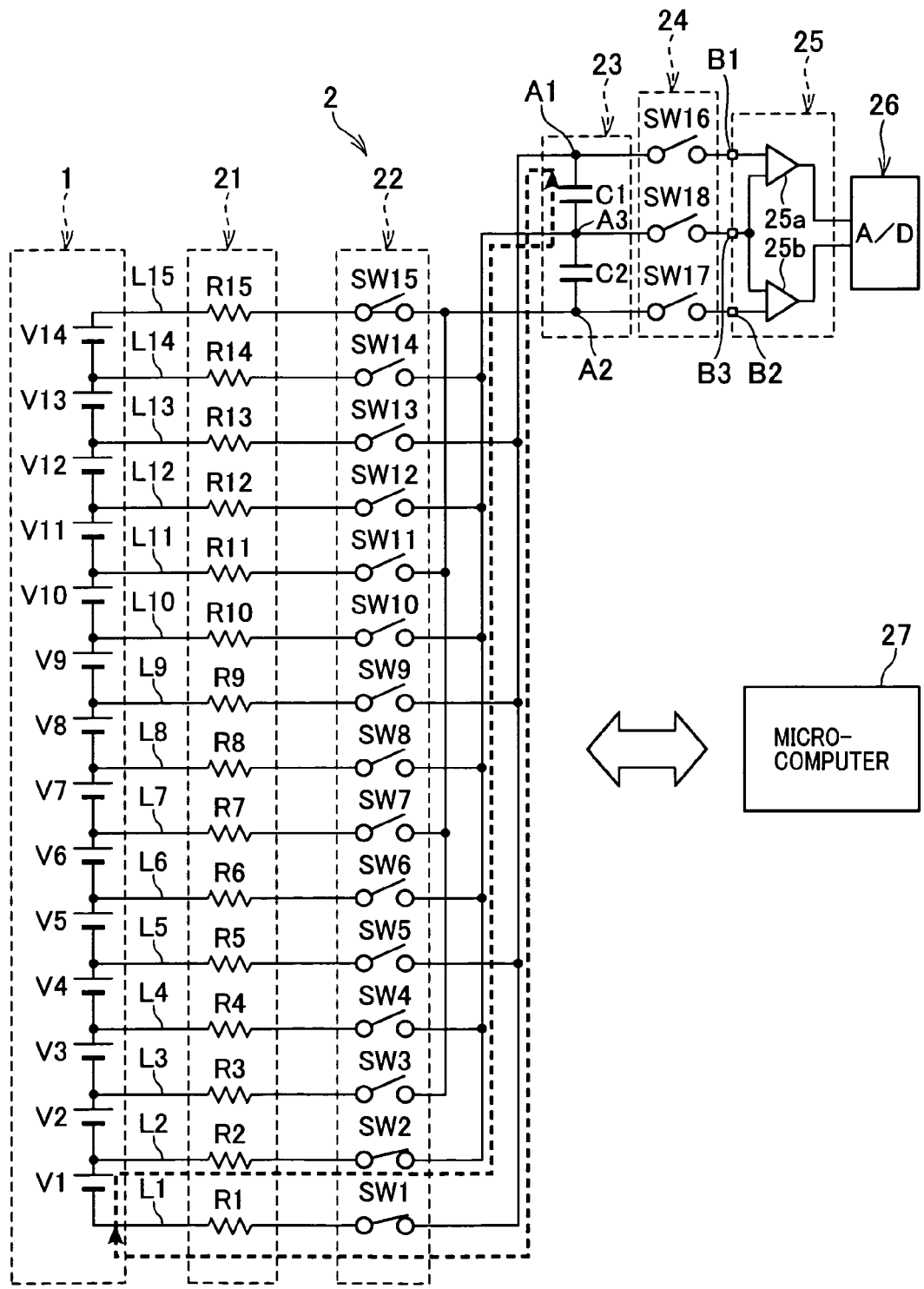
FIG. 4 is a circuit diagram explaining an operation in applying voltage of a battery cell to one of a pair of capacitors in the voltage monitoring device in FIG. 1.

Next, the voltage monitoring device 2 in the present embodiment, the following case is described. This is a case of performing disconnection detection for the detection lines L1 to L15, which are connected to the electrode terminal of the battery cells V1 to V14, by using one of the pair of capacitors C1 and C2 of the capacitor circuit 23. Referring to FIG. 4, an example of an operation in a case where disconnection detection for the detection line L1 connected to the electrode terminal of the battery cell V1 is performed by using the first capacitor is described in detail.

As shown in FIG. 4, the input side sampling switches SW1 and SW2 of the input side connection switching unit 22 are turned on by the instruction signal from the microcomputer 27. When the input side sampling switches SW1 and to SW2 are turned on, the first capacitor C1 is connected via the resistors R1 and R2 to the electrode terminal of the battery cell V1 to be charged, so that voltage of the first capacitor C1 is equal to that of the battery cell V1.

After that, the input side sampling switches SW1 and SW2 of the input side connection switching unit 22 are turned off and the output side sampling switches SW16 and SW18 of the output side connection switching circuit 24 are turned on for a predetermined duration of time by the instruction signal from the microcomputer 27.

When the output side sampling switches SW16 and SW18 are turned on, the first capacitor C1 is connected to the first differential voltage detection unit 2.5a via the first and third input terminals B1 and B3 of the potential difference detection circuit 25. The first differential voltage detection unit 25a amplifies voltage of the first capacitor C1, which is equal to that of the battery cell V1, to output the amplified voltage to the AD converter 26.

Then, the AD converter 26 converts the outputted signal from the first differential voltage detection unit 25a to the corresponding digital signal, and outputs the converted digital signals to the microcomputer 27.

Based on the outputted signals from the AD converter 26, the microcomputer 27 detects voltage of the battery cell V1, and compares the detected voltage of the battery cell V1 with the predetermined threshold value for determination to determine whether or not disconnection of the detection line L2, which is connected to the electrode terminal of the battery cell V1, is has occurred. For example, the microcomputer 27 determines that disconnection of the detection line L2 is not present (i.e., L2 is normal) if the detected voltage of the battery cell V1 is higher than the predetermined threshold value for determination, and determines that disconnection of the detection line L2 is present if the detected voltage of the battery cell V1 is equal to or lower than the predetermined threshold value for determination.

When disconnection detection for the battery cells V2 to V14 other than the battery cell V1 is performed, the pair of input side sampling switches among the input side sampling switches SW2 to SW15, which are connected to the battery cell which is a disconnection detection object among the battery cells V2 to V14, and the output side sampling switches among the output side sampling switch SW16 to SW18, which are connected to the capacitor charged with voltage of the battery cell that is a disconnection detection object, are controlled to be turned on and off by the instruction signal from the microcomputer 27. This makes it possible to output the digital signal indicating voltage of the battery cell which is a voltage detection object to the microcomputer 27.

Here, for example, when voltage of the battery cell V1 is charged in only one of the capacitors C1 and C2, the input side sampling switches SW1 and SW2 of the input side connection switching unit 22 are turned on to form a closed circuit in which the resistors R1 and R2 of the filter circuit 21 and the first capacitor C1 of the capacitor circuit 23 are connected in series to one another. Thus, current flows in this closed circuit as shown in a heavy dotted arrow in FIG. 4.

In this way, when voltage of the battery cell V1 is charged in only one of the pair of capacitors C1 and C2, a capacitance of the capacitors in the closed circuit is determined by a capacitance value of only one of the first and second capacitors C1 and C2, i.e., is not determined by harmonic mean of a capacitance value of the first capacitors C1 and a capacitance valued of the second capacitor C2. Thus, the total capacitance in the closed circuit does not become smaller.

On the other hand, in the present embodiment, the resistance value Rx of each of the resistors R2, R4, R6, R8, R10, R12, and R14 of the first resistor group, which is connected the connection point A3 between the first and second capacitors C1 and C2, is set to one half of the resistance value Ry of each of the resistors R1, R3, R5, R7, R9, R11, R13, and R15 of the second resistor group which is connected to the independent ends A1 and A2 (Rx=Ry/2). That is, the resistance value Rx of the resistor R2 of the first resistor group is smaller than the resistance value Ry of the resistor R1 of the second resistor group.

In this way, when voltage of the battery cell V1 is charged in only one of the pair of capacitors C1 and C2, a resistance in the closed circuit becomes smaller, thereby making it possible to shorten a time for the capacitor to be charged with voltage of the battery cell.

Figure 5:
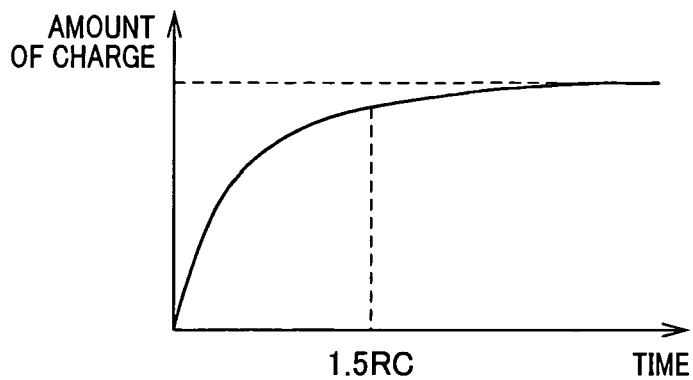
FIG. 5 is a graph explaining a time required for one of a pair of capacitors to be charged with voltage of a battery cell in the voltage monitoring device in FIG. 1

More specifically, in a case where voltage monitoring of the battery cell V1 using only one of the pair of capacitors C1 and C2, when the input side sampling switches SW1 and SW2 are turned on, as shown in FIG. 5, the capacitor is charged under a condition of time constant τ2 (=1.5RC). As shown in a formula in FIG. 5, this time constant τ2 is a value (=(R+R/2)×C=1.5RC) which is determined by multiplying a capacitance value (=C) of the first capacitor C1 by an addition value (=R+R/2=1.5R) which is determined by addition of a resistance value Ry (=R) of the resistor R1 of the second resistor group and a resistance value Rx (=R/2) of the resistor R2 of the first resistor group.

In the present embodiment, an example in which the capacitor C1 is charged with voltage of the battery cell V1 is explained. The same is applied to a case where only one of the pair of the capacitors C1 and C1 is used to charge the corresponding capacitor with voltages of the battery cells other than the battery cell V1. In this case, the capacitors C1 and C1 are charged under a condition of time constant τ2 (=1.5×RC) as described above.

Figure 6:
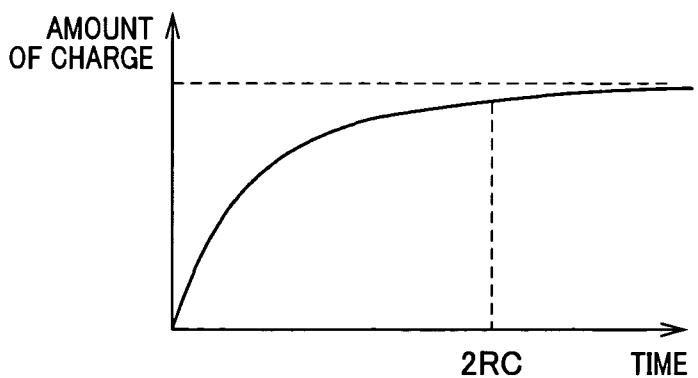
FIG. 6 is a graph explaining a time required for one of a pair of capacitors to be charged with voltage of a battery cell in a voltage monitoring device in a comparative example.

Here, FIG. 6 shows a comparative example in which all of the resistors R1 to R2 of the filter circuit 21 have the same resistance value (=R). In the comparative example, as shown in FIG. 6, the first capacitor C1 is charged under a condition of a time constant τ3 (=2RC). As shown in a formula in FIG. 6, this time constant τ3 is a value (=(R+R)×C=2RC) which is determined by multiplying a capacitance value (=C) of the first capacitor C1 by an addition value (=R+R=2R) which is determined by addition of a resistance value (=R) of the resistor R1 and a resistance value (=R) of the resistor R2.

In the voltage monitoring device 2 in the present embodiments explained above, among the plurality of the resistors R1 to R15, the resistance value Rx of each of the resistors R2, R4, R6, R8, R10, R12, and R14 of the first resistor group, which is connected the connection point end A3 between the first and second capacitors C1 and C2, is set to a value smaller than the resistance value Ry of each of the resistors R1, R3, R5, R7, R9, R11, R13, and R15 of the second resistor group which is connected to the independent ends A1 and A2. Specifically, the resistance value Rx of each of the resistors R2, R4, R6, R8, R10, R12, and R14 of the first resistor group is set to one half of the resistance value Ry of each of the resistors R1, R3, R5, R7, R9, R11, R13, and R15 of the second resistor group (Rx=Ry/2).

Thus, among the plurality of the resistors R1 to R15 of the filter circuit 21, the resistance value of the resistors of the first resistor group, which is connected to the connection point A3 between the capacitors C1 and C2, is designed to be smaller. This makes it possible to avoid a decrease in a filter function of the filter circuit 21, compared to a case where the resistance value of all of the resistors R1 to R15 becomes smaller.

In addition, when one of the capacitors C1 and C2 is charged with voltage of the battery cell, as the resistance value of the resistors of the first resistor group becomes smaller, a time for required for the capacitor to be charged with voltage of the battery cell can be more shortened.

Therefore, in the voltage monitoring device using the double flying capacitor method, a decrease in a filter function of each of the resistors can be improved, and a time for required for the capacitor to be charged with voltage of the battery cell can be shortened.

(Second Embodiment)

The voltage monitoring device 2 in the first embodiment can have pronounced effects in improving a decrease in a filter function of each of resistors and in shortening a time for required for the capacitor to be charged with voltage of the battery cell.

In the voltage monitoring device using the double flying capacitor method as explained above, a part of the input side sampling switches SW1 to SW15 may be short-circuited (short-circuit fault). In this case, when the capacitors C1 and C2 are charged with voltages of the battery cells V1 to V14 in order, a short circuit may occur between the detection lines so that a closed circuit is formed. If a short-circuit current flows in the closed circuit, the assembled battery 1 or the voltage monitoring device 2 may be damaged due to the short-circuit current.

Figure 7A:
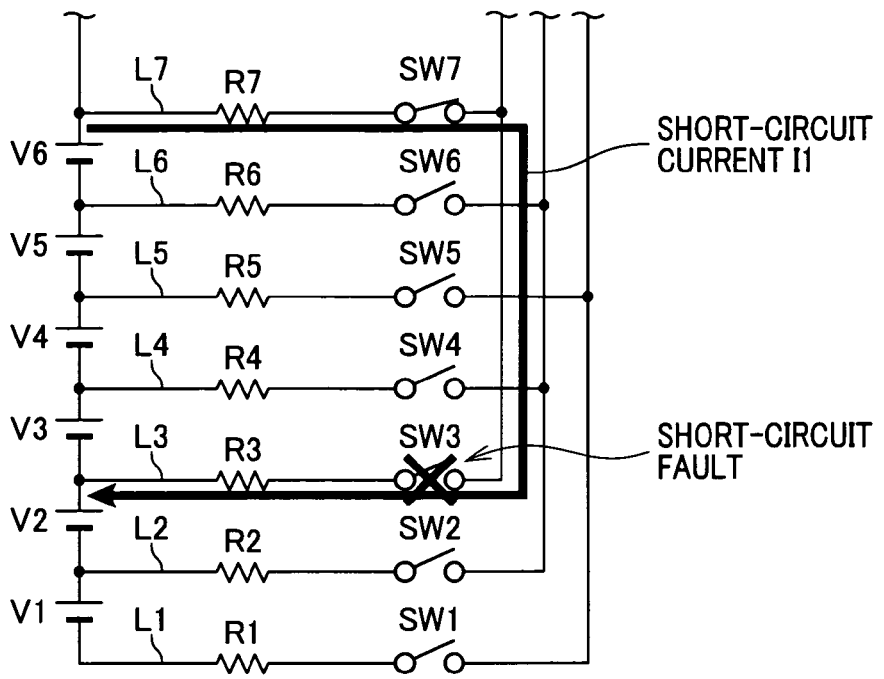
FIG. 7A is a partial circuit diagram explaining issues related to a short-circuit fault of an input side sampling switch SW3.
Figure 7B:
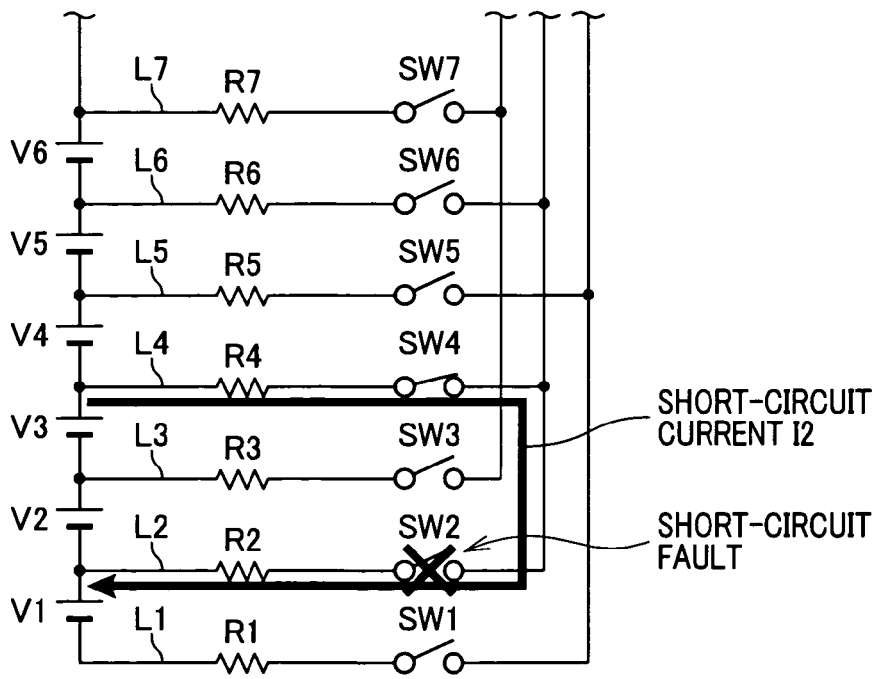
FIG. 7B is a partial circuit diagram explaining issues on a short-circuit fault of an input side sampling switch SW2.

FIGS. 7A and 7B show diagrams explaining issues that may arise when the input side sampling switches SW1 to SW15 are short-circuited. FIG. 7A shows an example where the input side sampling switch SW3 is short-circuited, and FIG. 7B shows an example where the input side sampling switch SW2 is short-circuited.

As shown in FIG. 7A, in a case where, among the input side sampling switches SW3, SW7, SW11, and SW15 connected to the independent end A2 of the second capacitor C2, the sampling switch SW3 is short-circuited, when the sampling switch SW7 is turned on, as shown in a heavy solid arrow in FIG. 7A, a short-circuit current I1 flows. This short-circuit current I1 and its power consumption W1 are expressed by I1=4×V/(R+R)=2V/R and W1=(4×V)²/(R+R)=8V²/R, respectively, where V denotes a voltage of each of the battery cells V1 to V4, and R denotes a resistance value of each of the resistors R3 and R7.

Here, in a case where the input side sampling switch SW3 is short-circuited, when the input side sampling switch SW11 is turned on, the number of the battery cells configuring a closed circuit increases, so that the short-circuit current becomes larger. This means that the short-circuit current I1 as explained above becomes a minimum current when any one of the input side sampling switches SW3, SW7, SW11, and SW15 is short-circuited.

Similarly, in a case where any one of the input side sampling switches SW1, SW5, SW9, and SW13, which are connected to the independent end A1 of the first capacitor C1, are short-circuited, when the input side sampling switch which is not short-circuited is turned on, short-circuit current which is equal to or larger than the short-circuit current I1 flows.

As shown in FIG. 7B, in a case where, among the input side sampling switches SW2, SW4, SW6, SW8, SW10, SW12, and SW14 connected to the connection terminal A3 between the first and second capacitors C1 and C2, the sampling switch SW2 is short-circuited, when the sampling switch SW4 is turned on, as shown in a heavy solid arrow in FIG. 7A, a short-circuit current I2 flows. This short-circuit current I2 and its power consumption W2 are expressed by I2=2×V/(R2+R/2)=2V/R and W2=(2×V)²/(R/2+R/2)=8V²/R, respectively, where V denotes a voltage of each of the battery cells V1 to V4, and 2/R denotes a resistance value of each of the resistors R2 and R4. This means that the short-circuit current I2 is equal in current value to the short-circuit current I1. The short-circuit current I2 becomes a minimum current when any one of the input side sampling switches SW2, SW4, SW8, SW10, SW12, and SW14 is short-circuited.

Figure 8A:
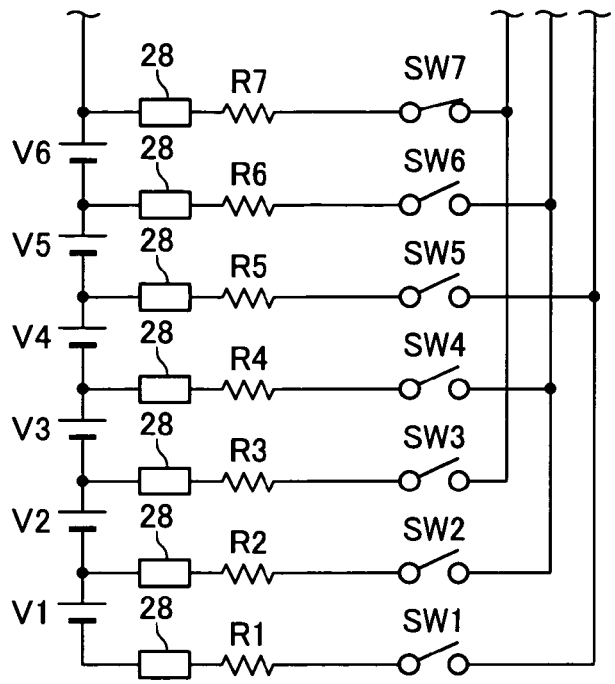
FIG. 8A is a partial circuit diagram of a voltage monitoring device with protection elements connected between battery cells and resistors of a filter circuit, according to a second embodiment of the present invention.
Figure 8B:
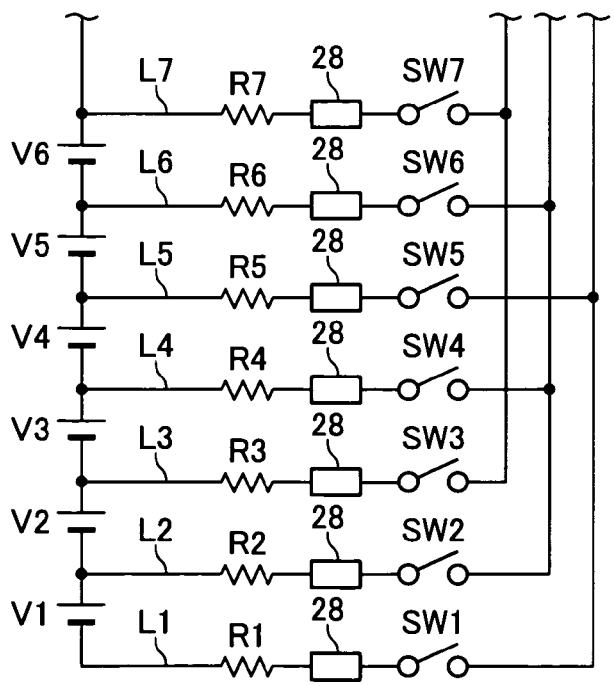
FIG. 8B is a partial circuit diagram of a voltage monitoring device with protection elements connected between resistors of a filter circuit and input side sampling switches, according to a second embodiment of the present invention.

In order to solve such issues as explained above, the voltage monitoring device 2 in the second embodiment is provided with a plurality of protection elements 28, which are able to be disconnected when short-circuit current arises, is connected between each of the resistors R1 to R15 of the filter circuit 21 and each of the battery cells V1 to V14 as shown in FIG. 8A, or between each of the resistors R1 to R15 of the filter circuit 21 and each of the input side sampling switches SW1 to SW15 of the input side connection switching unit 22 as shown in FIG. 8B.

Each of the protection elements 28 is configured by an element that is able to be disconnected when current which is equal to or larger than the short-circuit current I1 (=short-circuit current I2) flows. Specifically, it is preferable to use an element such as a fuse that is able to be opened when a short circuit of the input side sampling switches occurs. In the filter circuit 21 of the second embodiment, as described in the first embodiment, each resistor of the second resistor group has the same resistance value, and each resistor of the first resistor has a resistance value that is designed to be one half of the resistance value of each resistor of the second resistor group.

According to the present embodiment as explained above, the voltage monitoring device 2 is provided with the plurality of protection elements 28, which are able to be disconnected when short-circuit current arises, is connected between each of the resistors R1 to R15 of the filter circuit 21 and each of the battery cells V1 to V14 (see FIG. 8A), or between each of the resistors R1 to R15 of the filter circuit 21 and each of the input side sampling switches SW1 to SW15 of the input side connection switching unit 22 (see FIG. 8B). Due to this, when at least one of the input side sampling switches SW1 to SW15 is short-circuited (short-circuit fault), the corresponding protection element is disconnected. This makes it possible to prevent the assembled battery 1 or the voltage monitoring device 2 from being damaged due to the short-circuit current.

In addition, each resistor of the second resistor group has the same resistance value, and each resistor of the first resistor has a resistance value that is designed to be one half of the resistance value of each resistor of the second resistor group.

According to this, short-circuit current, which flows when a part of the input side sampling switches SW1 to SW15 is short-circuited (short-circuit fault), has the same minimum current value. Therefore, each of the protection elements can be configured by an element that is able to be disconnected when the same short-circuit current flows.

(Modifications)

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

For example, the embodiments described above may be modified as follows.

(1) In the above-described embodiments, it is preferable that a resistance value Rx of each resistor of the first resistor group, which is connected to the connection point A3 between the capacitor C1 and C2, is designed to be approximate one half of a resistance value Ry of each resistor of the second resistor group (Rx≈Ry/2), for the purpose of ensuring filter performance of the filter circuit 21 or the like. However, the resistance values Rx and Ry are not limited to this.

For example, the resistance value Rx of each resistor of the first resistor group, which is connected the connection point end A3 between the first and second capacitors C1 and C2, may be arbitrarily set under a condition that the resistance value Rx of each resistor of the first resistor group is designed to be smaller than the resistance value Ry of each resistors of the second resistor group which is connected to the independent ends A1 and A2. In this case, each resistor of the first resistor group might not have the same resistance value, but may have different resistance value.

(2) In the above-described embodiments, when disconnection detection for the battery cells V1 to V14 is performed, voltage of each of the battery cells is monitored by using one of the pair of capacitors C1 and C2. The present disclosure is not limited to this. For example, when the number of battery cells is an odd number, voltage of a battery cell of an end number (e.g., when thirteen battery cells V1 to V13 connected in series to one another are used, among them, the battery cell V13 corresponds to the battery cell of the end number) may be monitored by using one of the pair of capacitors C1 and C2.

(3) In the above-described embodiments, the following case is described. This is a case where, when disconnection detection for the battery cells V1 to V14 is performed, one of the pair of capacitors C1 and C2 is charged with voltage of the battery cell which is a disconnection detection object, and subsequently, among the output side sampling switches SW16 to SW18, the output side sampling switch, which is connected to the capacitor charged with voltage of the battery cell which is a disconnection detection object, is turned on. The present disclosure is not limited to this. For example, all of the output side sampling switches SW16 to SW18 may be turned on.

(4) In the above-described embodiments, an example in which the voltage monitoring device 2 is applied to the assembled battery 1 configured by 14 battery cells connected in series to one another is described. The present disclosure is not limited to this. For, example, an object to which the voltage monitoring device 2 is applied is not limited to the number of battery cells.

(5) In the above-described embodiments, the following plurality of protection elements is described. The protection elements, which are able to be disconnected when short-circuit current arises, are connected between each of the resistors R1 to R15 of the filter circuit 21 and each of the battery cells V1 to V14, or between each of the resistors R1 to R15 of the filter circuit 21 and each of the input side sampling switches SW1 to SW15 of the input side connection switching unit 22. The present disclosure is not limited to this.

For example, each of the resistor R1 to R15 of the filter circuit 21 may be configured by a resistance element (e.g., chip resistor, diode). In this case, each of the resistors R1 to R15 of the filter circuit 21 may also function as the protection element for the short-circuit fault.

According to this, when a part of when a part of the input side sampling switches SW1 to SW15 of the input side connection switching unit 22 is short-circuited (short-circuit fault), the corresponding resistance element is disconnected. This makes it possible to prevent the assembled battery 1 or the voltage monitoring device 2 from being damaged due to the short-circuit current.

In addition, each of the resistors R1 to R15 of the filter circuit 21 also functions as the protection element for the short-circuit fault. This makes it possible to protect the assembled battery 1 or the voltage monitoring device 2 from being damaged due to the short-circuit fault without increasing parts count.

(6) In the above-described embodiments, it is preferable the voltage monitoring device 2 is configured to monitor voltage of each of the battery cells V1 to V14 by using the pair of capacitors C1 and C2. The present disclosure is not limited to this. For example, the voltage monitoring device 2 may be configured to monitor voltage of each of the battery cells V1 to V14 by using three or more capacitors. The voltage monitoring device 2 with such a configuration can obtain the same operation and effect as described in the above embodiments, under a condition that a resistor (first resistor group), which is connected to a connection point between the capacitors, is smaller in resistance value than a resistor (second resistor group) which is connected to an independent end of the capacitors.

(7) In the above-described embodiments, the voltage monitoring device 2 is applied to an in-vehicle high voltage battery, but is not limited to this, for example, may be applied to the other batteries.

What is claimed is:

1. A voltage monitoring device for monitoring voltage of each of battery cells connected in series to one another to configure an assembled battery, comprising:
    a capacitor circuit that includes a plurality of capacitors connected in series to one another;
    a filter circuit that includes a plurality of resistors connected to an electrode terminal of each of the battery cells;
    an input side connection switching unit that connects the electrode terminal of each of the battery cells to an independent end of the plurality of capacitors and a connection point between adjacent capacitors among the plurality of capacitors via the filter circuit to apply voltage of each of the battery cells to the capacitors, the independent end being a contact point that does not connect the adjacent capacitors, the connection point being a contact point that connects the adjacent capacitors;
    a potential difference detection unit that includes a plurality of input terminals and detects a potential difference between the plurality of input terminals; and
    an output side connection switching unit that connects the independent end of the plurality of capacitors and the connection point between the adjacent capacitors to the plurality of input terminals to apply charged voltage of at least one capacitor among the plurality of input terminals to the plurality of input terminals of the potential difference detection unit, wherein:
    the plurality of resistors is divided into a first resistor group and a second resistor group;
    the first resistor group is connected to the connection point between the adjacent capacitors;
    the second resistor group is connected to the independent end of the plurality of capacitors; and
    a resistance value of the first resistor group is smaller than a resistance value of the second resistor group.

2. The voltage monitoring device according to claim 1, wherein:
    the plurality of capacitors of the capacitor circuit is configured by a pair of capacitors connected in series to each other.

3. The voltage monitoring device according to claim 1, wherein:
    the resistance value of the first resistor group is one half of the resistance value of the second resistor group.

4. The voltage monitoring device according to claim 1, wherein:
    the input side connection switching unit includes a plurality of input side sampling switches which are connected between the plurality of resistors of the filter circuit and the plurality of capacitors of the capacitor circuit.

5. The voltage monitoring device according to claim 4, further comprising:
    a plurality of protection elements that are disconnected when current equal to or more than a short-circuit current flows in the voltage monitoring device.

6. The voltage monitoring device according to claim 5, wherein:
    each of the protection elements is connected between each of the battery cells and each of the resistors or between each of the resistors and each of the input side sampling switches.

7. The voltage monitoring device according to claim 4, wherein:
    each of the resistors is configured by a resistance element which functions as a protection element that is disconnected when current equal to or more than a short-circuit current flows in the voltage monitoring device.

8. The voltage monitoring device according to claim 1, wherein:
    the output side connection switch unit includes a plurality of output side sampling switches which are connected between the plurality of capacitors of the capacitor circuit and the plurality of input terminals of the potential difference detection circuit.

9. The voltage monitoring device according to claim 1, further comprising:
    a microcomputer that controls an operation of the input side connection switching unit and the output side connection switching unit.

10. A battery voltage monitoring system comprising:
    an assembled battery that is configured by a plurality of battery cells connected in series to one another; and
    a voltage monitoring device that monitors voltage of each of the battery cells,
    the voltage monitoring device including:
        a capacitor circuit that includes a plurality of capacitors connected in series to one another;
        a filter circuit that includes a plurality of resistors connected to an electrode terminal of each of the battery cells;
        an input side connection switching unit that connects the electrode terminal of each of the battery cells to an independent end of the plurality of capacitors and a connection point between adjacent capacitors among the plurality of capacitors via the filter circuit to apply voltage of each of the battery cells to the capacitors, the independent end being a contact that does not connect the adjacent capacitors, the connection point being a contact that connects the adjacent capacitors;
        a potential difference detection unit that includes a plurality of input terminals and detects a potential difference between the plurality of input terminals; and
        an output side connection switching unit that connects the independent end of the plurality of capacitors and the connection point between the adjacent capacitors to the plurality of input terminals to apply charged voltage of at least one capacitor among the plurality of input terminals to the plurality of input terminals of the potential difference detection unit, wherein:
    the plurality of resistors is divided into a first resistor group and a second resistor group;
    the first resistor group is connected to the connection point between the adjacent capacitors;
    the second resistor group is connected to the independent end of the plurality of capacitors; and
    a resistance value of the first resistor group is smaller than a resistance value of the second resistor group.

* * * * *